United States Patent [19]

Koehler et al.

[11] 4,311,039

[45] Jan. 19, 1982

[54] DISC CENTRIFUGE PHOTOSEDIMENTOMETER

[76] Inventors: Mark E. Koehler, 16775 Elderdale Dr., Middleburg Heights, Ohio 44130; Theodore Provder, 26320 Hickory La., Olmsted Falls, Ohio 44138; Richard A. Zander, 5506 Haverhill Dr., Parma, Ohio 44129

[21] Appl. No.: 93,996

[22] Filed: Nov. 14, 1979

[51] Int. Cl.³ .......................................... G01N 15/02
[52] U.S. Cl. .................................. 73/61.4; 73/432 PS
[58] Field of Search ......................... 73/61.4, 432 PS; 318/11, 12, 13

[56] References Cited

U.S. PATENT DOCUMENTS

| | | | |
|---|---|---|---|
| 1,635,314 | 7/1927 | Doignon | 318/11 |
| 2,489,725 | 11/1949 | Rutemiller | 318/12 |
| 2,886,986 | 5/1959 | Kopp . | |
| 3,173,273 | 3/1965 | Fulton . | |
| 3,208,229 | 9/1965 | Fulton . | |
| 3,243,106 | 3/1966 | Atherton et al. | 73/432 PS X |
| 3,399,934 | 9/1968 | Kopp . | |
| 3,418,939 | 12/1968 | Kopp . | |
| 3,475,968 | 11/1969 | Jones | 73/432 PS |

OTHER PUBLICATIONS

Report CR 77-6, "Design and Construction of Disc Centrifuge Photosedimentometer", by Zander et al., Apr. 13, 1977.

Primary Examiner—James J. Gill

[57] ABSTRACT

An apparatus is provided which is characterized by a motor, a transmission, e.g., a continuously variable ratio friction transmission, and apparatus for interrupting power to the motor for a precise interval of time. A particular utilization of this device is for a photosedimentometer to enable more accurate determinations of particle size and size distribution.

10 Claims, 7 Drawing Figures

DISC CENTRIFUGE PHOTOSEDIMENTOMETER

BACKGROUND OF THE INVENTION

This invention pertains to a rotating disc photosedimentometer useful in determining particle size and size distribution. In particular, this invention, by precisely controlling transmission of torque to the rotating disc, enables reproducible conditions needed for consistent and meaningful sample analysis. Heretofore, rotating disc photosedimentometers have been provided in which test conditions were subject to substantial variation and nonreproducibility due to the imprecise control of the electric motor applying torque to the rotating disc.

U.S. Pat. No. 3,475,968 discloses a method and apparatus for determining particle size and distribution, and also a method for using that apparatus to carry out the centrifugal analysis of particle size and size distribution. To conduct such an analysis by the rotating disc method, it is essential in one particular experimental method to establish a continuous density gradient in a liquid medium composed of two fluids, a spin fluid and a buffer fluid. Because the buffer fluid is less dense than the spin fluid and is injected after all the spin fluid, it is necessary to cause partial mixing of the fluids to establish the continuous density gradient. This partial mixing is accomplished by overriding the speed control of the electric motor, which in turn causes a rapid positive or negative acceleration of short duration in the rate of rotation of the disc centrifuge. The speed control is overridden by manually pushing a button for a specified amount of time. The period of time the button is pushed controls the length of motor control override and hence the period of partial mixing. Because the period of partial mixing varies from run to run, the continuous density gradient also varies. Hence, reproducibility of results is difficult to obtain.

There is therefore, a need for a rotating disc photosedimentometer which provides for precisely controlled and consistent periods of partial mixing to produce consistent continuous density gradients, and thereby assure reproducibility and reliability of results. Since these devices are of especial utility in control of latex production on a commercial scale, the need for such accuracy can be readily appreciated.

BRIEF STATEMENT OF THE INVENTION

The present invention provides a photosedimentometer useful in determining particle size and size distribution. The apparatus utilizes a hollow disc permeable to radiant energy and which has an opening in one face for the introduction of samples into the hollow interior. The disc is symmetrical and balanced about an axis, and is mounted for high speed rotation about that axis, said axis being disposed in either a horizontal or vertical attitude. For higher speed determinations, the horizontal axis of rotation attitude is normally used. For slower speeds, i.e., equal to or less than about 800 rpm., the vertical axis of rotation attitude is used. The apparatus further has a motor that is actuated by a driving force for causing rotation of the disc about the axis at a predetermined selectable speed. Preferably, the motor operates at a constant speed. Connecting the disc to the motor is a continuously variable ratio friction drive transmission. This transmission, which may be automatically adjustable and is conveniently manually adjustable as to output shaft speed, enables the rotation of the drive motor to be transmitted to the disc at a selectable speed of rotation. Finally, the apparatus contains means for interrupting the driving force to the motor for a preselected precise interval. After the power-off interval, the motor substantially instantaneously resumes its speed of rotation to again rotate said disc at said predetermined speed.

The apparatus may be used with other photosedimentometer procedures including a homogeneous start method, the creaming method, and the frontal chromatography method.

BRIEF DESCRIPTION OF THE DRAWINGS

The present invention may be better understood by having reference to the annexed drawings showing a preferred embodiment of the present invention and wherein.

DETAILED DESCRIPTION OF THE DRAWINGS

Figure 1:
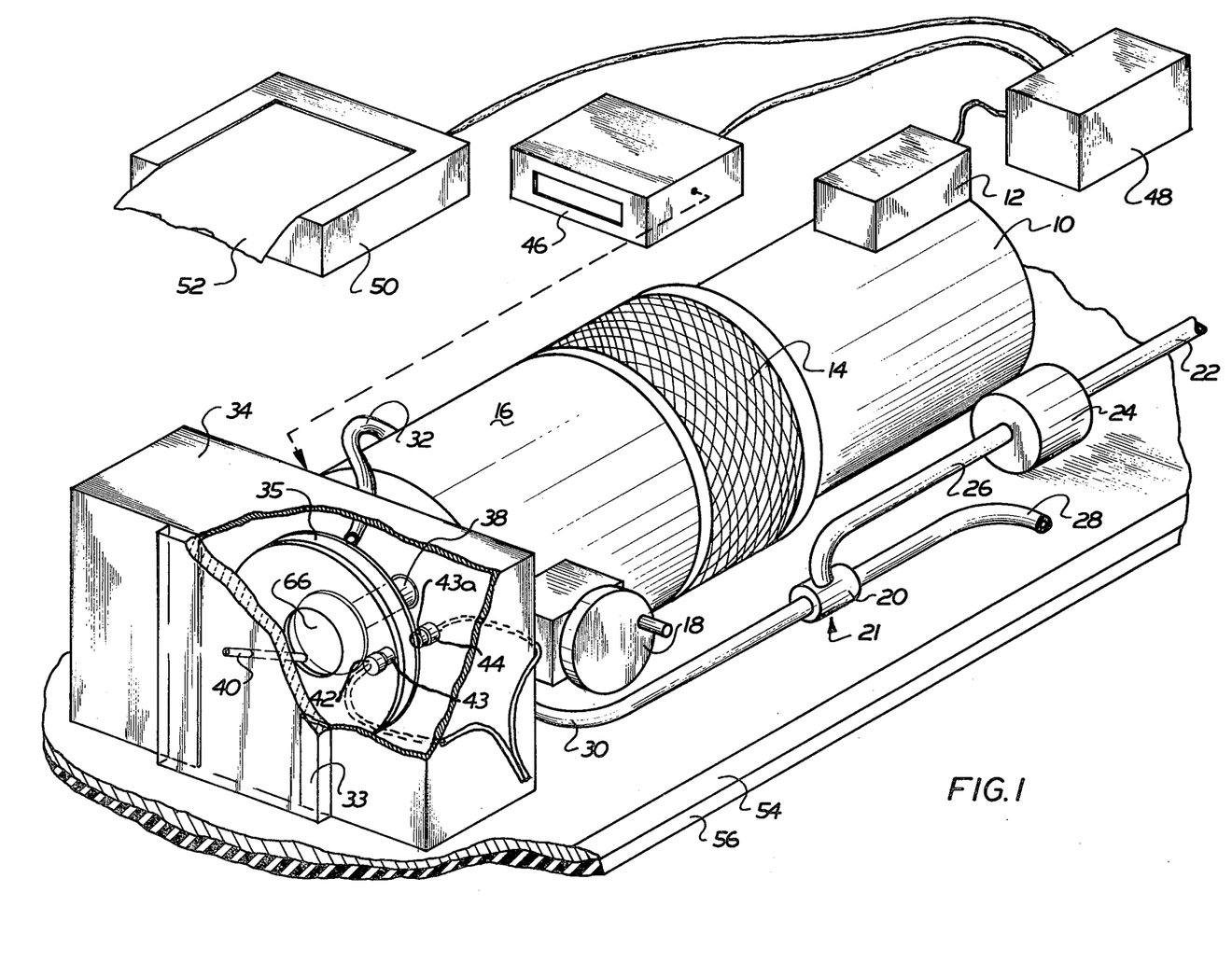
FIG. 1 is an isometric illustration partially cut away and partially diagrammatic, and illustrating a photosedimentometer apparatus in accordance herewith.

FIG. 1 is an isometric view of a preferred embodiment of the apparatus of this invention. Referring to FIG. 1, the numeral 10 designates a motor, and in this preferred case, an electric motor 10 receives its driving force, in this case electric power, through a capacitor mechanism 12 associated with the motor. Motor 10 is conveniently a standard commercially available ½ horsepower AC motor. Such a motor is desirably much oversized for rotating a 6" plastic disc, but its size assures constant speed of the motor and virtually instantaneous recovery of speed after current is reapplied as will be explained below. The motor 10 is connected by any suitable known flexible coupling to the input shaft of a known continuously variable ratio friction drive transmission 16. A safety cage 14 is provided as a shroud about the coupling. In this instance, the transmission 16 is a Koppers Series "R" adjustable speed drive, of the type described and shown U.S. Pat. Nos., 2,886,986; 3,399,934; and 3,418,939. Transmission 16 is adjusted by wheel 18 in order to vary the transmission ratio between input and output speed. In the present device, the transmission is arranged in the apparatus so that the speed of the output shaft is greater or lesser than the speed at the input shaft. Thus, whereas an electric motor 10 will rotate at 1800 rpm., the disc 35 may be rotated at speeds from about 1200 up to 11,000 rpm. Contemplated use of the present device would be where the speed at the output shaft 38 is greater than the speed at the input shaft.

In order to minimize adverse thermal effects on the test results, transmission of heat generated in the transmission 16 is kept to a minimum. The oil reservoir within the housing of the transmission 16 is, therefore, conveniently cooled by a suitable oil cooler 21. In the preferred embodiment, there is used an air cooler 20 of the vortex type such as shown and described in U.S. Pat. No. 3,654,768 (See also U.S. Pat. Nos. 3,173,273 and 3,208,229). The cooler 21 is supplied with air from an independent source (not shown). The air from said source flows through line 22 to an air filter 24 where contaminants are removed. Line 26 connects the air filter 24 to the vortex generator 20. Due to the action of this type of cooler 21, hot air is exhausted away from the cooler 21 by line 28. The cooling air from the cooler 21 is connected by line 30 to any suitable high surface area heat exchanger (not shown) immersed in the oil sump of transmission 16. The heat exchanger inside transmission 16 is connected to exhaust line 32. Exhaust line 32 carries the used cool air to a point inside of housing 34 for maintenance of the temperature within the disc housing 34 at a substantially constant temperature. The positive pressure provided by this arrangement prevents airborne contaminants from entering the disc housing 34.

Housing 34 encloses the hollow disc 35, which is conveniently formed from a machinable or moldable plastic or resinous material transparent to the light source, e.g., Plexiglas (polymethyl methacrylate) or the like. Disc 35 is connected to shaft 38 which is the output shaft of the transmission 16. Torque applied to output shaft 38 from transmission 16 causes disc 35 to rotate at a controlled rate. Particle containing samples to be tested, and also the buffer and spin fluids are introduced into disc 35 through injection port 40. Injection port 40 is adapted to receive the needle of a conventional laboratory syringe. Such injection port 40 is disposed to introduce liquid into disc 35, through the opening 66 at a point displaced from the center of rotation of said disc 35, so that the liquid so introduced is subjected to centrifugal forces urging it away from the center of the disc 35.

Fixedly disposed on one side of disc 35 and spaced therefrom is radiant energy source 42. Preferably this radiant energy source is an electric lamp. Disposed on the opposite side of disc 35 and spaced therefrom is a suitable radiant energy detector 44. Support for the source 42 and the detector 44 is provided by the housing 34. When radiant energy source 42 is a lamp, detector means 44 is commonly a photoreceptor, or photo electric cell. A collimator 43, 43a each portion having a vertically disposed slit is provided to confine the light on either side of the disc 35 to a small area and the area read to a small portion of the arc created by the band of particles. A tachometer 46 senses and displays the speed of rotation. One known form of tachometer pick up device or sensor (not shown) includes a gear member mounted on the shaft 38 coacting with a Hall effect pick up, the impluses generated by the gear teeth during rotation being electronically converted by known means to a digital readout of speed by the apparatus 46.

Figure 1A:
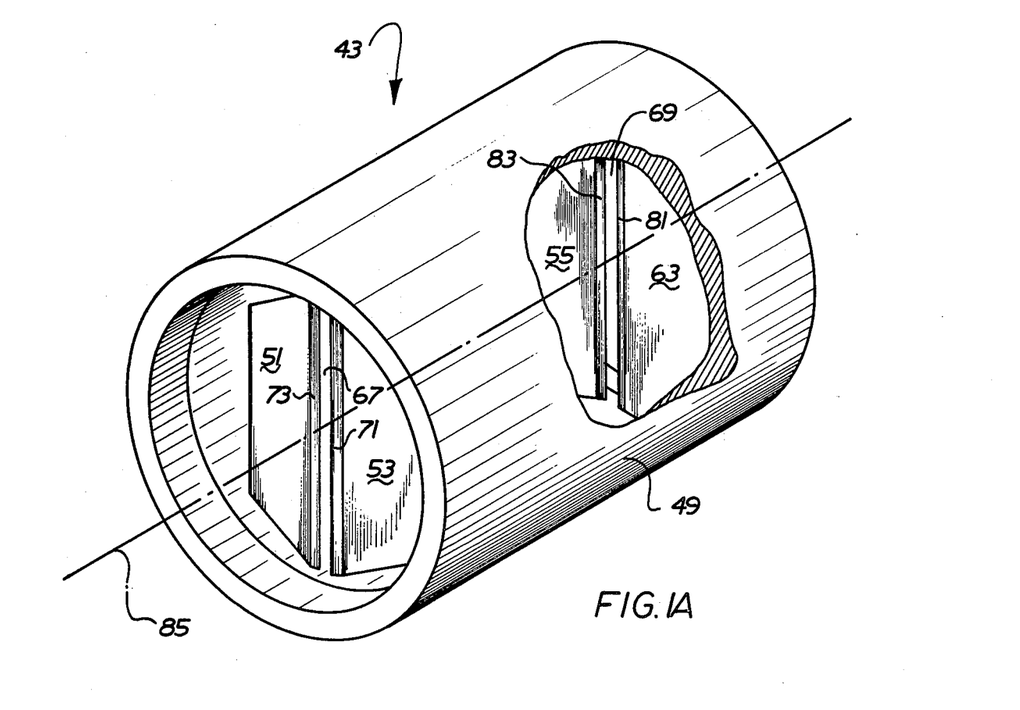
FIG. 1a is a partially cut away perspective view of a light collimator assembly useful on either side of the hollow disc of FIG. 2.

A preferred collimator assembly is shown in FIG. 1a. A pair of two-slit collimator units, 43, 43a one of which is shown in FIG. 1a, is disposed substantially as shown in FIG. 1 at 43, 43a. Each unit 43, (43a) includes in the preferred embodiment a tubular body 49 having razor sharp members 51, 53, 55, and 63 each axially spaced pair defining the axially spaced slits 67, and 69. Thus, members 51 and 53 define entry slit 67, and members 55 and 63 define exit slit 69. The edges 71 and 73 are vertically disposed, razor sharp, and serve as the vertical boundaries of slit 67. Likewise the edges 81 and 83 are razor sharp and serve as the vertical boundaries of slit 69. Thus, two of the units as shown in FIG. 1a are disposed on the same longitudinal axis 85 and with the outer portion of the disc 35 interposed between the units 43 and 43a and intercepting said axis 85. The light source 42 and the detector 44 or photocell 44 are also coaxial with the units 43, 43a and external of the units 43, 43a relative to the outer portion of the disc 35. Thus, as the band or bands of particles (as hereinafter described) move radially outwardly in the spin fluid, they will intercept a beam of collimated light and change the intensity which change is detected by the detector 44.

In order to provide the necessary change in acceleration there is provided a programmable timer 48. The time 48 controls the application of the driving force, e.g., electric power, to motor 10 and capacitor assembly 12. Information received from detector means 44, is transmitted to a recording means 50. Recording means 50 is a known recording device which generates a trace across a moving sheet of chart paper 52.

The electric motor 10, transmission 16, and housing 34 are all securely mounted by bolts onto a base plate 54. For cushioning the base plate 54, there is conveniently provided a layer of foam rubber which is effective to reduce noise and vibration during operation.

Figure 2:
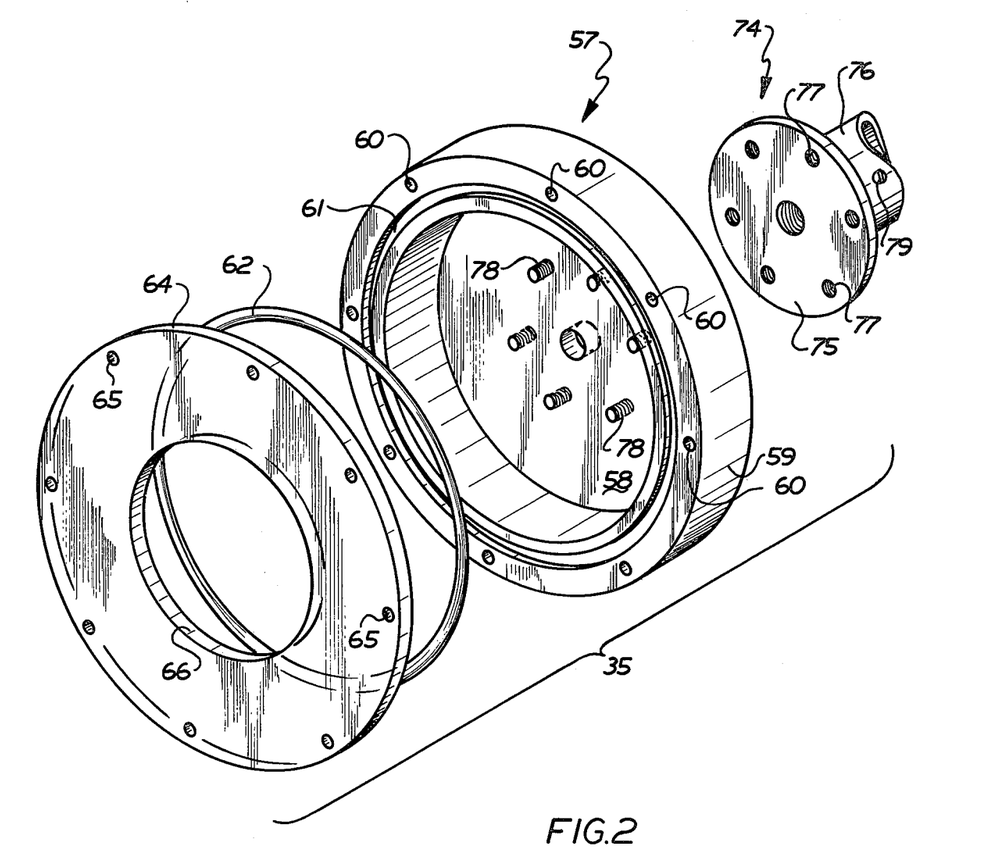
FIG. 2 is an exploded isometric view of a hollow disc useful in the apparatus shown in FIG. 1.

FIG. 2 is an exploded view of a hollow disc 35 useful in the apparatus of the present invention. It is not substantially different from that shown in British Pat. No. 895,222 or U.S. Pat. No. 3,243,106. The disc assembly 35 includes a cup member 57, and apertured cover plate 64 and a mounting hub 74. The cup member 57 is of generally cylindrical configuration having a closed end face 58. The axially extending side wall 59 is suitably drilled and tapped, as at uniformly circumferentially spaced points 60, to accept fastening means for holding the cover plate 64 in place. To provide a suitable seal between the cover plate 64 and the hollow cylindrical body 57, there is provided an annular groove 61 dimensioned to receive an O-ring 62 for sealing engagement between the cup body 57 and the cover 64. The cover 64 is suitably drilled as at 65 to accept fasteners for threaded engagement with the holes in the sidewall 59 of the cup 57. The cover 64 is also provided with a central opening 66 to enable introduction into the hollow interior of the disc 35 of liquid materials as will be described below.

In order to mount the disc on the output shaft of the transmission 16, there is provided a mounting hub 74 including a mounting plate 75 and an integral sleeve 76. The mounting plate 75 is suitably drilled as at 77 to accept fasteners adapted to threadedly engage uniformly circumferentially spaced drilled and tapped holes 78. The sleeve 76 may be provided with a set screw 79 to aid in anchoring the disc to the output shaft 38 of the transmission 16. In some embodiments, a keyway and key of known structure may be utilized in combination with a set screw, or separately therefrom, to secure the hub and disc to the shaft 38. Reference may be had to FIG. 1 of U.S. Pat. No. 2,886,986 for a disclosure of a key and keyway shaft connector to a hub. Alternatively, the sleeve portion 76 may be threadedly engaged on a threaded shaft 38. The means of securing the disc to the output shaft 38 is unimportant so long as the disc is secure in its mounting thereon. Obviously, the disc 35 and its mounting on the shaft 38 must be carefully balanced to prevent vibration.

A principal feature of the present invention is in the provision of a programmable timer 48 which interrupts the power source, e.g., electricity to the drive motor 10, for an accurate and reproducible period of time and replaces the manual interrupt system of the prior art devices.

Figure 3:
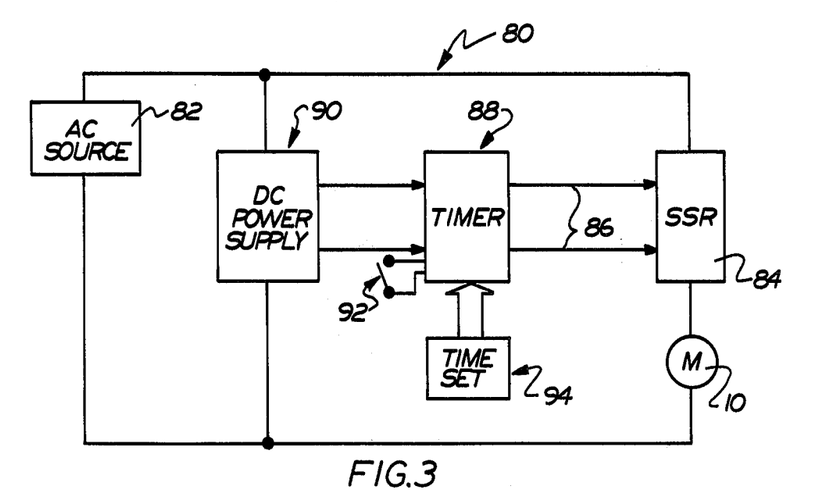
FIG. 3 is a block diagram of a motor control circuit, including a timer circuit for momentarily interrupting power to the motor.

FIG. 3 is a block diagram of a motor control circuit including a timer circuit for momentarialy interrupting power to the motor.

Accordingly, there is illustrated in FIG. 3 a circuit 80 for controlling supply of electric power to the motor 10 which supplies the driving force for rotating the disc 35. The motor 10 is supplied with power from an AC source 82, which may be a conventional wall outlet, and is interconnected in series with a solid state relay 84 across the source 82. The solid state relay 84 is a semiconductor device and may be visualized as simply a pair of contacts which will be open or closed depending upon the state of the control signal supplied to the solid state relay 84 along control lines 86 by a timer circuit, generally indicated at 88. When a high logic level signal is supplied across the control lines 86, solid state relay 84 will be "closed", and power will be supplied to the motor 10 from the AC source 82. The motor 10 will then operate, causing rotation of the disc at a substantially constant preselected rate. When a control signal applied across lines 86 is at a low logic level, however, the solid state relay 84 will be "open", thereby interrupting the supply of power to the motor 10 from the AC source 82.

The control signal applied across control lines 86 is generated by a programmable timer, or "cut" timer generally indicated at 88. This timer is illustrated in FIG. 3 as including a DC power supply circuit 90, connected across the AC source 82, to provide a DC supply voltage to a solid state relay 84. The timer 88 normally provides a high logic level signal across control lines 86, thereby causing the solid state relay 84 to be closed. Thus, power will normally pass unimpeded through the solid state relay 84 to energize the motor 10 in the fashion described previously.

Upon the depression and release of a momentary contact pushbutton 92, however, the control signal supplied by timer 88 along control line 86 will drop to a low logic level for a precisely controlled interval, thereby interrupting the supply of power to the motor 10 for that same interval of time. The length of this interval will be set by a "time set" circuit 94 which may, for example, comprise a series of conventional thumbwheel switches. Both the time set switches 94 and the momentary contact pushbutton 92 will be mounted on a control panel and will thus be accessible to the operator for actuation. In operation, the operator will first set the thumbwheel switches 94 to a value corresponding to the desired duration of power interruption. Then, at the appropriate time the operator will depress and then release the momentary contact pushbutton 92. Upon the release of the pushbutton 92, the timer circuit 88 will initiate operation and open the solid state relay 84 for an interval of time corresponding to the interval set into the thumbwheel switches 94. Accuracy of reproducibility of the set time interval in the timer circuit is measured in milli-seconds. The combination of precise timing of the interruption of power to the motor, the constant speed at the drive means, and the precise control over disc speed afforded by the transmission 16 and their unique coaction enables in the improved sedimentometers hereof the execellent reproducibility and reliability of results.

Figure 4:
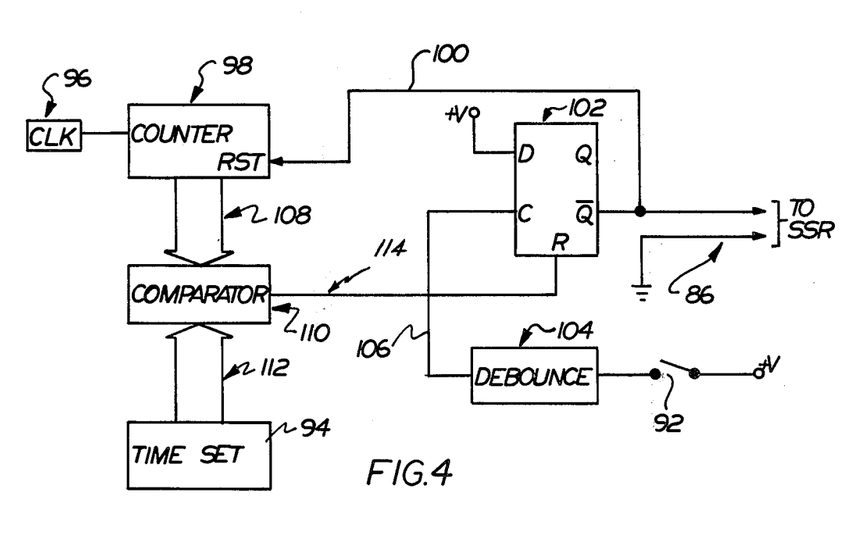
FIG. 4 is a more detailed block diagram of one form which the timer utilized in FIG. 3 may take.

FIG. 4 illustrates one form which the timer circuit 88 of FIG. 3 may take. Generally speaking, the timer circuit of FIG. 4 operates to measure a time interval by counting the number of cycles of a regularly occuring clock signal. In FIG. 4, a clock circuit 96 (which may, for example, the crystal controlled to provide a high degree of stability) provides the clock signal. A counter circuit 98 counts these clock signals and will thus accumulate a count which will increase in direct proportion in the length of time that it has been counting.

Normally, counter circuit 98 is held in a reset (zeroed) condition by a reset signal supplied along reset line 100, derived from the $\overline{Q}$ output of a type "D" flip-flop 102. The momentary contact pushbutton 92 is connected to the clock input of this flip-flop 102 through a debounce circuit 104. The purpose of this debounce circuit 104 is to provide a single, well defined pulse for each depression of switch 92. Thus, when the momentary contact pushbutton 92 is depressed and then released, a single pulse will be provided to the clock input of flip-flop 102 along line 106. The output signal provided at the $\overline{Q}$ output thereof will then drop from a high logic level to a low logic level, thereby removing the reset signal from the counter 98 and permitting it to begin accumulating a count.

The count contained within counter 98 will be provided along output lines 108 to a comparator 110, which will compare this count with the count preset by thumbwheel switches 94 and supplied to the comparator 110 along lines 112. When the count contained within counter 98 equals the count set by thumbwheel 94, the comparator 110 (which may, for example, be a series of "exclusive-or" logic gates) will provide a pulse along output line 114 to the reset input of flip-flop 102, thereby causing the $\overline{Q}$ output thereof to return to a high logic level. This once again forces the counter 98 into a reset condition, preparing it for the next depression of the momentary contact pushbutton 92 by the operator.

From the foregoing it will be appreciated that the length of time that the $\overline{Q}$ output of flip-flop 102 is at a low logic level will correspond with the length of time that it takes the counter 98 to count up to the count preset into the thumbwheel switches 94 by the operator. If, for example, the clock circuit 96 is calibrated so that one clock pulse is provided every milli-second, then the count contained within the counter 98 will correspond to the number of milli-seconds which have elapsed since the momentary contact pushbutton 92 was released. Since the $\overline{Q}$ output of flip-flop 102 will only be low until this count has reached the count set into the thumbwheel switches 94, the number of milli-seconds that $\overline{Q}$ output is at a low logic level will correspond to this preset count, and may be simply increased or decreased by changing the setting of the thumbwheel switches 94. Thus, the operator has precise control over the length of time that a low logic level signal is provided at the $\overline{Q}$ output of flip-flop 102. Since this signal controls the solid state relay 84 of FIG. 3, it will produce a correspondingly timed interruption in the supply of power to the motor 10. Alternately, the solid state relay may be controlled using the $\overline{Q}$ output of flip-flop 102 to sink current from a voltage source through the control section of the solid state relay to provide a motor "on"

condition when $\bar{Q}$ is at a low logic level and a motor "off" condition when $\bar{Q}$ is at a high logic level condition. The output at $\bar{Q}$ may be pulled up to the supply voltage across a resistor to insure that there is no current flow through the control section of the solid state relay when the output $\bar{Q}$ is at a high logic level condition. This alternate configuration is implemented in FIG. 6.

Figure 5:
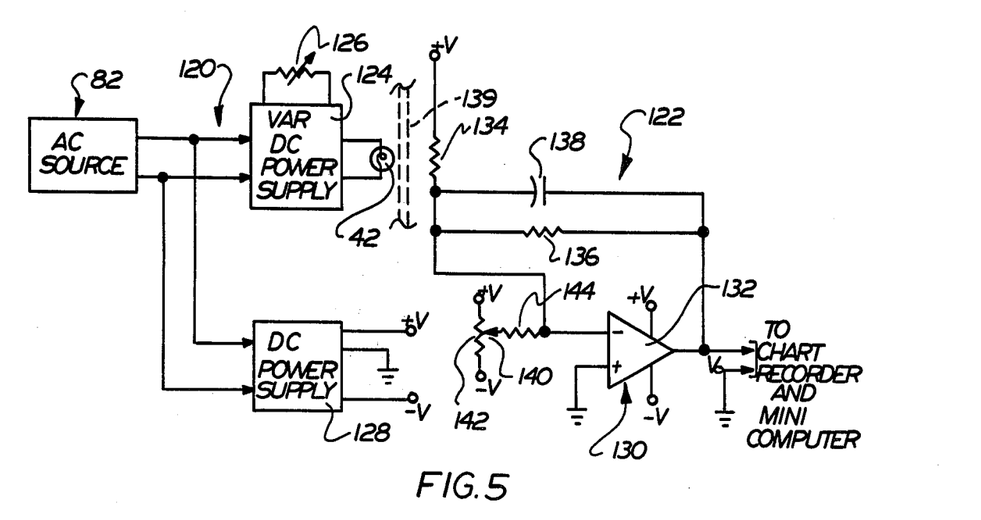
FIG. 5 is a schematic diagram of circuitry for detecting the changes in radiant energy transmissiveness at a specific radial location on the rotating disc.

Referring now to FIG. 5, there is illustrated a circuit for detecting changes in the optical transmissivity of the fluid contained within the cavity of the rotating disc 35. This circuit includes essentially two subsystems, the photo source 120, and photo detector 122. Each of these two subsystems has a respectively associated DC power supply, both powdered by AC source 82.

The photo source 120 includes a variable DC power supply 124. The actual light source comprises a lamp 42 (also FIG. 1) connected across the output of DC power supply 124. The amount of light emitted by the lamp 42 is operator controllable by varying a potentiometer 126 associated with DC power supply 124. By adjusting this control 126, the magnitude of the voltage provided across the lamp 42 is changed, thereby changing the intensity of light emitted by the lamp 42. Preferably, this DC power supply 124 will have a preset current limit to protect the lamp 42 from current surges (as when it is first switched on), and thereby lengthen its useful life.

The photo detector 122 similarly includes its own DC power supply 128, which will in this case provide fixed positive and negative voltages $+V$ and $-V$, both referenced to a common ground, for powering an amplifier circuit generally indicated at 130.

The amplifier circuit 130 generally includes a conventional operational amplifier 132, having its noninverting input connected to ground, and its inverting input connected to the negative voltage supply $(-V)$ through a photosensitive resistor 134. Also connected to the inverting input of the amplifier 132 is a feedback resistor 136 which couples this input back to the output of the amplifier 130. A capacitor 138 is connected across feedback resistor 136, in order to provide high frequency filtering of the output signal. The output voltage $V_0$ provided at the output of amplifier 132 will depend upon the ratio of the resistances of resistors 134 and 136. If this ratio changes, then the output voltage will change in a corresponding manner. Although resistor 136 has a fixed resistance, resistor 134 has a resistance which will, at any given time, depend upon the level of light from light source 42 impinging thereon.

The resistor 134 will be physically positioned adjacent the lamp 42, but will be spaced somewhat apart from it by a gap 139. Located within this gap 139 will be the fluid containing cavity of the spinning disc 35. Suitable baffles, e.g., slits, are provided in housing 34 so that the light can be transmitted from lamp 42 to resistor 134 through only a selected radial location along the disc 35. The amount of this light reaching the resistor 134 from the lamp 42 will depend upon the transmissiveness of the fluid contained within the cavity of the spinning disc at that radial location. As this transmissiveness changes due, for example, to passage radially of a band of particles through the spin medium, the level of light and thus the resistive value of resistor 134 will similarly change, producing a corresponding change in the output signal $V_0$ of the amplifier 130.

The DC level of the output signal $V_0$ may be established by a bias signal taken from the wiper arm 140 of potentiometer 142, and supplied to the inverting input of the amplifier 132 through an input resistor 144. The operator can change the DC level of the output signal $V_0$ by adjusting the location of the wiper arm 140 along potentiometer 142.

The output signal $V_0$ provided by the photo detector 122 will be provided to a chart recorder, e.g., recorder 50 FIG. 1), mini computer, or other appropriate recording, and/or analysis equipment.

Figure 6:
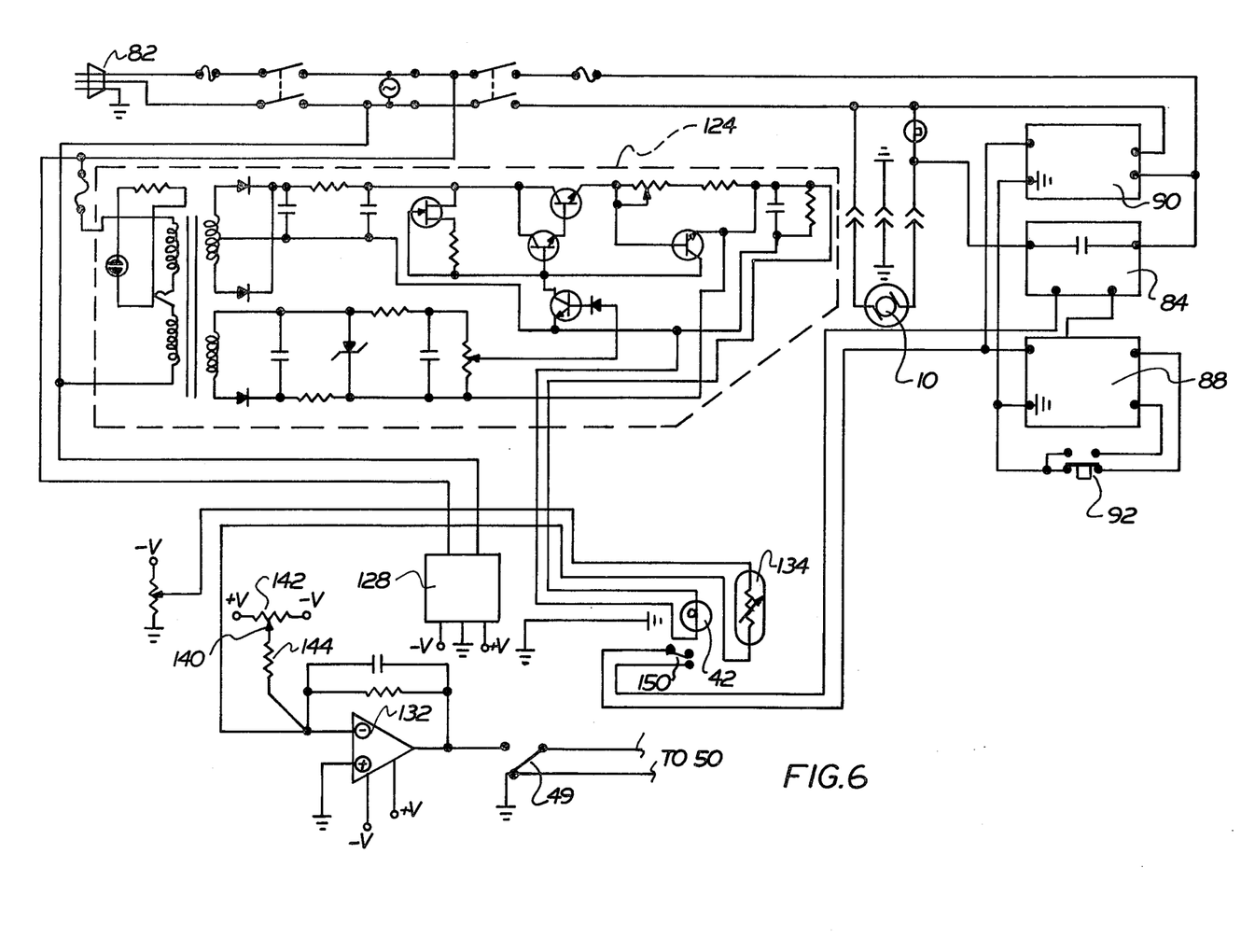
FIG. 6 is an electrical schematic of the control unit shown in FIG. 1, and incorporating the subcircuits shown in FIGS. 3, 4, and 5.

FIG. 6 is an electrical circuit schematic diagram for the control unit 48 shown in FIG. 1 with the subcircuits shown in FIGS. 3, 4, and 5 indicated by appropriate numbers in FIG. 6 and is generally self-explanatory. The power supply 124 is shown in greater detail and is a commercially available unit. The switch 150 is associated with the housing 34 so that if the door 33 is opened during operation, the motor shuts down.

The manner of using the apparatus of the present invention is as follows:

A spin fluid which is usually deionized water which may contain a suitable surfactant, such as, potassium tripolyphosphate (KTPP), to the extent of 0.5 g./100 ml. $H_2O$ (mixed by ultrasound) and a buffer solution which is usually a 50% deionized water—50% methanol solution are prepared. If surfactant is used in the spin fluid, it may also be used in the buffer solution at the same concentration. These solutions must be free of contamination, for example, from using improperly cleaned glassware.

Test samples are prepared in 50% (by volume) methanol-water solution. For large particle size of $1.0\mu$, one drop of sample at 50% solids in 25 ml. of the 50% MeOH-$H_2O$ solution is usually sufficient. If the particle size is smaller, e.g., $0.3\mu$, 3 to 6 drops are used. The test solutions are mixed with ultrasound. Test samples should be run within 5 minutes of preparation.

The lamp and detector system 42-44 (FIG. 1) usually requires about 1 hour to warm up properly. After this, the motor 10 is energized and the various units, e.g., the tachometer 46, energized. The desired rpm as displayed on the digital tachometer is selected with the control handle 18. Compressed air is introduced into the vortex cooler. 20 ml. of spin fluid free of air bubbles is smoothly injected into the hollow disc 35 through the tube 40 with a 30 ml. syringe. The cut time is set in the manually operated selector 94. Using a 1 ml. syringe, 1 ml. of buffer is added to the spinning disc 35 in the same manner as the spin fluid.

The cut switch 92 (FIG. 3) is then depressed to initiate the power interrupt interval. The following table gives representative "cut" times.

TABLE I

| RPM | Spin Fluid Volume (ml) | Cut Time (Sec) |
| --- | --- | --- |
| 1,000 | 20 | — |
| 2,000 | 20 | .3 |
| 3,000 | 20 | — |
| 4,000 | 20 | .3 |
| 5,000 | 20 | — |
| 6,000 | 20 | .25 |
| 7,000 | 20 | — |
| 8,000 | 20 | .6 |
| 9,000 | 20 | — |
| 10,000 | 20 | — |

The recorder 50 is properly zeroed with zeroing switch 49 as shown in FIG. 6 so that the instrument 50 zero will correspond with the electrical zero when the pen reads zero millivolts observed as "0" units on the chart paper.

The instrument 50 is also adjusted to read 10 units at 100 millivolts.

The apparatus is then ready to receive a test sample. ¼ ml. of the sample latex prepared as above is injected into the rotating disc. Particles of latex will usually segregate according to particle size into well defined bands which travel radially through the spin medium. Passage there through will interrupt a collimated beam of light from lamp 42 causing a change in the output of the photodetector 44 and a corresponding movement of the pen on the recorder 50. The location, amplitude and shape of peaks in the trace of the pen on the graph paper 52 is indicative of the particle size and size distribution of the particles in the sample.

The apparatus should be carefully cleaned after each test.

"Streaming" is a condition that sometimes occurs in making photosedimentometer measurements. Although this condition is obviated for the most part in the improved apparatus, it may appear. The condition manifests itself as a random, finger-like coursing of the sample through the spin medium (spin fluid and buffer) visible with a stroboscope. This usually requires a new sample and operational conditions. An overconcentrated sample will usually stream. Poor fluid delivery contributes to streaming. A poor buffer gradient will cause streaming. The main damaging effect of streaming is that the percentage of undersized fractions is less than it should be for a given size range due to the smaller particles being drawn into the spin fluid by the larger particles. Thus, the distribution curve will show a much coarser particle separation. This results in decreased resolution (band broadening). Adjustment in speed of rotation may be required to reduce the incidence of streaming.

Experience has shown that replicate tests show a remarkable uniformity in results. It is believed that the combination of the precisely controllable output shaft speed (i.e., within 1 or 2 rpm at 4000 rpm) afforded by the traction type transmission and the precise control over the time during which the power is cut when preparing the spin medium makes this apparatus highly reliable and useful as a production control device for the production of dispersions such as, paint latices.

The foregoing description of a mode of using the improved device hereof is a preferred mode of use and is intended to be illustrative. Other fine particle compositions (micron and submicron) sizes may also be analyzed by the apparatus hereof and in such cases different spin media may be used. Those skilled in the use of photosedimentometers will be able to use these devices in determining particle size and size distribution, benefiting, however, from the improved structure and reliability thereof as herein described.

What is claimed is:

1. A photosedimentometer apparatus useful in determining particle size and size distribution of submicron size particles comprising:

a hollow cylindrically shaped disc permeable to radiant energy and having an opening in the front face thereof for injection of liquid to the interior of said disc;

a motor actuatable by a driving force and operative for rotating said disc, said motor being operable at a substantially constant speed;

a continuously variable ratio friction drive transmission coacting between said motor and said disc for rotating said disc in response to rotation of said motor and at a selectable speed of rotation in the range of from 1200 to 11000 rpm, accurate to within 1 or 2 rpm at 4000 rpm, said transmission having an input shaft directly coupled to said motor and an output shaft, said transmission including means for selecting a predetermined speed of rotation of said output shaft, and said disc being secured to said output shaft;

a radiant energy source disposed on one side of said disc and spaced therefrom;

a detector disposed on the opposite side of said disc and spaced therefrom in radiant energy receiving relation to said source; said source and detector being located adjacent the periphery of said disc;

means for collimating the radiant energy from said source; and means for interrupting said driving force to said motor for a preselected interval of time measured through an electronic clock circuit including a clock source for producing clock pulses of constant duration and means for counting said pulses up to a preset value, and after said interval of time, substantially instantaneously regaining said substantially constant speed of said motor and reestablishing substantially the same selectable speed of rotation of said disc.

2. An apparatus as defined in claim 1 wherein the output of said transmission is directly attached to a centrifugal disc, said centrifugal disc being permeable to radiant energy.

3. An apparatus as defined in claim 1 wherein the interrupting means includes means for varying the duration of said interval.

4. An apparatus as defined in claim 1 including a solid state relay coacting between said interrupting means and said motor to discontinue and reapply said driving force to said motor.

5. An apparatus as defined in claim 1 wherein the means for interrupting said driving force for a predetermined interval of time includes a programmable timer.

6. An apparatus as defined in claim 1 including an electric light source disposed on one side of said disc and a photodetector disposed on the opposite side thereof adjacent the outer periphery of said disc.

7. An apparatus as defined in claim 6 including means for collimating light emanating from said light source.

8. An apparatus as defined in claim 6 wherein the disc is a hollow disc permeable to radiant energy having an opening in one circular face for injection of liquid into the interior thereof.

9. An apparatus as defined in claim 1 including means for cooling said transmission.

10. An apparatus as defined in claim 9 wherein the cooling means is an air vortex tube cooler.

* * * * *